United States Patent
Shoshi et al.

[11] Patent Number: 5,486,438
[45] Date of Patent: Jan. 23, 1996

[54] ELECTROPHOTOGRAPHIC PHOTOCONDUCTOR

[75] Inventors: Masayuki Shoshi, Yokohama; Masakatsu Shimoda, Higashikurume; Akiko Konishi, Tokyo; Megumi Kawahara, Yokohama; Akio Kojima, Mitaka; Tetsuro Suzuki; Masao Yoshikawa, both of Yokohama, all of Japan

[73] Assignee: Ricoh Company, Ltd., Tokyo, Japan

[21] Appl. No.: 262,271

[22] Filed: Jun. 20, 1994

Related U.S. Application Data

[63] Continuation of Ser. No. 18,445, Feb. 16, 1993, Pat. No. 5,350,653.

[30] Foreign Application Priority Data

Mar. 2, 1992 [JP] Japan ................................. 4-080487
May 20, 1992 [JP] Japan ................................. 4-154548

[51] Int. Cl.$^6$ ........................... G03G 5/09; G03G 5/047
[52] U.S. Cl. ........................... 430/58; 430/59; 430/83
[58] Field of Search ........................... 430/58, 59, 83

[56] References Cited

U.S. PATENT DOCUMENTS 4,184,871 1/1980 Oba et al. ................................. 430/83
4,407,919 10/1983 Murayama et al. ........................ 430/58

FOREIGN PATENT DOCUMENTS 20334 2/1978 Japan ................................. 430/83
173747 10/1983 Japan ................................. 430/58
7956 1/1984 Japan ................................. 430/58
287570 11/1989 Japan ................................. 430/58

*Primary Examiner*—Roland Martin
*Attorney, Agent, or Firm*—Oblon, Spivak, McClelland, Maier, & Neustadt

[57] ABSTRACT

An electrophotographic photoconductor is composed of an electroconductive substrate, and a photoconductive layer formed thereon, which contains a charge generating material, and a vinylidene compound of formula (I):

$$Ar-CH=\underset{\underset{X}{|}}{C}-X \quad \text{with CN above C} \quad (I)$$

wherein Ar represents an aromatic group; and X represents cyano group, an alkyl group having 1 to 8 carbon atoms, or an alkoxycarbonyl group represented by $-COOC_nH_{2n+1}$, in which n is an integer of 1 to 8; or a vinylidene compound of formula (II):

$$Ar-CH=C(COOR)_2 \quad (II)$$

wherein Ar represents an aromatic group; and R represents an alkyl group having 1 to 8 carbon atoms, which may form a ring in combination of two of the alkyl groups, each of these vinylidene compounds serving as a charge transporting material.

22 Claims, 2 Drawing Sheets

大,486,438

ELECTROPHOTOGRAPHIC PHOTOCONDUCTOR

This is a continuation of application Ser. No. 08/018,445, filed on Feb. 16, 1993, now U.S. Pat. No. 5,350,653.

BACKGROUND OF THE INVENTION

1. Field of the Invention

The present invention relates to an electrophotographic photoconductor, and more particularly to an electrophotographic photoconductor which comprises a vinylidene compound serving as a charge transporting material.

2. Discussion of Background

Conventionally, an inorganic photoconductive material such as selenium, selenium-tellurium alloy, or zinc oxide has been widely used for a photoconductive layer of an electrophotographic photoconductor. Recently, studies of electrophotographic photoconductors comprising organic photoconductive materials are made, and some of them are used in practice. Of the above-mentioned organic electrophotographic photoconductors, laminate-type electrophotographic photoconductors are mostly put to practical use, in which photoconductors a photoconductive layer comprises a charge generation layer and a charge transport layer. Owing to such a function-separating photoconductive layer, there is improvement in the photosensitivity and the life span of the photoconductor comprising the organic material, which are conventionally regarded as disadvantageous as compared with the photoconductor comprising the inorganic material. Therefore, the electrophotographic photoconductors comprising the organic photoconductive material have been actively developed, with taking full advantage of the merits for the organic photoconductive material, that is, low cost, safety and diversity.

The above-mentioned laminate-type electrophotographic photoconductor generally comprises an electroconductive substrate, arid a charge generation layer comprising a charge generating material such as a pigment or a dye, and a charge transport layer comprising a charge transporting material such as hydrazone or pyrazoline, which layers are successively overlaid on the electroconductive substrate. The charge transporting material contained in the charge transport layer is an electron-donor material, so that the above-mentioned photoconductor is of positive-hole-transfer type. Therefore, when the surface of the photoconductor is negatively charged, it exhibits the photosensitivity. However, corona discharge is unstable when used for negatively charging the photoconductor as compared with when used for positively charging the same. The amount of ozone or nitrogen oxides generated in the course of negative charging by the corona discharge is about 10 times that generated in the course of positive charging. Those products are attached to the surface of the photoconductor, so that the photoconductor physically and chemically deteriorates. Furthermore, those products cause the environmental problem.

In addition to the above-mentioned problems, to carry out the development of the negatively-chargeable photoconductor, a positive toner is necessitated. However, from the viewpoint of a triboelectric series, it is difficult to produce such a toner having a positive polarity as can be used with ferromagnetic carrier particles. In a two-component high-resistivity magnetic brush development method, therefore, negatively-chargeable toner is more stable and can be more freely selected and used as compared with the positively-chargeable toner. In this regard, a positively-chargeable photoconductor is more advantageous and can be more widely used than the negatively-chargeable photoconductor.

With the above-mentioned advantages of the positively-chargeable photoconductor taken into consideration, there are proposed positively-chargeable photoconductors comprising the organic photoconductive materials. For example, it is proposed that a charge transporting material having a high electron-transporting capability such as 2,4,7-trinitro-9-fluorenone be contained in a charge transport layer when the photoconductor is formed by laminating a charge transport layer on a charge generation layer. However, this compound has carcinogenicity, so that the above-mentioned photoconductor is extremely unsuitable for use in practice from the viewpoint of industrial hygiene.

Moreover, U.S. Pat. No. 3,615,414 discloses a positively-chargeable photoconductor comprising a thiapyrylium salt serving as a charge generating material which forms an eutectic complex by combining with polycarbonate serving as a binder resin. However, the above-mentioned photoconductor has the shortcoming that a memory phenomenon tends to occur, and therefore ghost images are easily obtained.

It is possible to prepare a positively-chargeable photoconductor with a laminate-type photoconductive layer in such a configuration that a charge generation layer comprising a charge generating material which can generate a positive hole or electron when the photoconductor is exposed to light, is formed on a charge transport layer which contains a charge transporting material capable of transporting the positive-hole or electron. However, in the above-mentioned structure of the positively-chargeable photoconductor, the charge generation layer becomes a surface layer, so that the charge generating material, which is fragile to external influences, for example, the application of short wavelength light such as ultraviolet light for light exposure, corona discharge, humidity, mechanical friction, inevitably exists in the surface portions of the photoconductor. As a result, electrophotographic properties deteriorate during the preservation of the photoconductor and the image formation process. Consequently, the quality of the obtained images is decreased.

On the other hand, the conventional negatively-chargeable photoconductor comprising a charge transport layer serving as a surface layer formed on a charge generation layer is scarcely subjected to the above-mentioned external influences. Rather, the charge transport layer formed on the charge generation layer has an effect of protecting the charge generation layer.

In the positively-chargeable photoconductor, it is proposed to provide on a charge generation layer comprising a charge generating material a thin protective layer comprising, for example, an insulating, transparent resin to protect the charge generation layer from the aforementioned external influences. However, when the photoconductor is exposed to light, there is a difficulty in efficiently generating electric charges in the charge generation layer because the light applied to the charge generation layer is intercepted by the protective layer. Therefore, the effect of light application is decreased. Furthermore, in the case where the thickness of the protective layer is large, the photosensitivity of the photoconductor deteriorates.

As mentioned above, various proposals for obtaining the positively-chargeable photoconductors have been made, but they have many problems with regard to the photosensitivity, the memory phenomenon or the industrial hygiene.

SUMMARY OF THE INVENTION

It is therefore an object of the present invention to provide an electrophotographic photoconductor which comprises an electroconductive substrate and a photoconductive layer formed thereon, comprising a charge generating material and a charge transporting material, with high photosensitivity and high durability.

The above-mentioned object of the present invention can be achieved by an electrophotographic photoconductor comprising an electroconductive substrate, a photoconductive layer formed thereon, comprising a charge generating material, and a vinylidene compound of formula (I):

$$Ar-CH=\overset{CN}{\underset{|}{C}}-X \quad (I)$$

wherein Ar represents an aromatic group; and X represents cyano group, an alkyl group having 1 to 8 carbon atoms, or an alkoxycarbonyl group represented by $-COOC_nH_{2n+1}$, in which n is an integer of 1 to 8; or a vinylidene compound of formula (II):

$$Ar-CH=C(COOR)_2 \quad (II)$$

wherein Ar represents an aromatic group; and R represents an alkyl group having 1 to 8 carbon atoms, which may form a ring in combination of two of the alkyl groups, each of these vinylidene compounds serving as a charge transporting material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
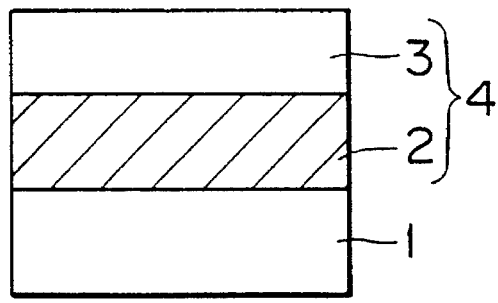
FIG. 1 is a schematic cross-sectional view showing a first example of an electrophotographic photoconductor according to the present invention.

The electrophotographic photoconductor of the present invention comprises an electroconductive substrate, and a photoconductive layer formed thereon, comprising a charge generating material, and a vinylidene compound of formula (I):

$$Ar-CH=\overset{CN}{\underset{|}{C}}-X \quad (I)$$

wherein Ar represents an aromatic group; and X represents cyano group, an alkyl group having 1 to 8 carbon atoms, or an alkoxycarbonyl group represented by $-COOC_nH_{2n+1}$, in which n is an integer of 1 to 8; or a vinylidene compound of formula (II):

$$Ar-CH=C(COOR)_2 \quad (II)$$

wherein Ar represents an aromatic group; and R represents an alkyl group having 1 to 8 carbon atoms, which may form a ring in combination of two of the alkyl groups, each of these vinylidene compounds serving as a transporting material.

When Ar represents an aromatic group in the above-mentioned formula (I) or (II), specific examples of the aromatic group are phenyl group; a polycyclic aromatic group such as naphthalene group, phenanthrene group, anthracene group or pyrene group; a heterocyclic aromatic group such as indole group, pyridine group, furan group, thiazole group, carbazole group or quinoline group; and a metallocene group such as ferrocene.

The aromatic group represented by Ar in the formulas (I) and (II) may have a substituent.

Specific examples of the substituent of the aromatic group represented by Ar in the formula (I) or (II) are amino group such as N,N-dimethylamino group, N,N-diethylamino group, N,N-dibenzylamino group, N,N-diphenylamino group, N,N-ditolylamino group, or N-tolyl-N-phenylamino group; an alkoxyl group having 1 to 8 carbon atoms such as methoxy group, ethoxy group or benzyloxy group; hydroxyl group; an alkyl group having 1 to 8 carbon atoms such as methyl group, ethyl group, butyl group, t-butyl group or trifluoromethyl group; a halogen atom such as fluorine, chlorine or bromine; an alkoxycarbonyl group represented by $-COOC_nH_{2n+1}$, wherein n is an integer of 1 to 8, such as methoxycarbonyl group, ethoxycarbonyl group, or butoxycarbonyl group; cyano group; and nitro group.

Specific examples of the vinylidene compounds of formulas (I) and (II) according to the present invention are shown in the following Tables 1 and 2. The present invention, however, is not limited by these compounds.

TABLE 1

$$Ar-CH=\overset{CN}{\underset{|}{C}}-X \quad (I)$$

| Compound No. | X | Ar |
|---|---|---|
| 1 | —CN | 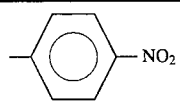—NO₂ |

TABLE 1-continued
$$Ar-CH=\underset{\underset{X}{|}}{C}-CN \qquad (I)$$
| Compound No. | X | Ar |
|---|---|---|
| 2 | —CN | 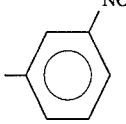 4-NO$_2$-C$_6$H$_4$— |
| 3 | —CN |  4-CN-C$_6$H$_4$— |
| 4 | —CN | 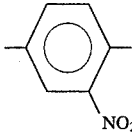 4-Cl-3-NO$_2$-C$_6$H$_3$— |
| 5 | —CN |  4-Cl-C$_6$H$_4$— |
| 6 | —CN | 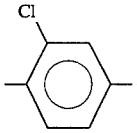 2,4-Cl$_2$-C$_6$H$_3$— |
| 7 | —CN | 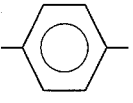 4-Br-C$_6$H$_4$— |
| 8 | —CN |  C$_6$H$_5$— |
| 9 | —CN | 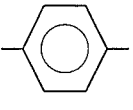 4-COCH$_3$-C$_6$H$_4$— |
| 10 | —CN |  4-COC$_2$H$_5$-C$_6$H$_4$— |
| 11 | —CN |  4-C$_2$H$_5$-C$_6$H$_4$— |
| 12 | —CN |  4-C$_4$H$_9$-C$_6$H$_4$— |
| 13 | —CN |  4-CF$_3$-C$_6$H$_4$— |

TABLE 1-continued
$$Ar-CH=C\underset{X}{\overset{CN}{|}} \quad (I)$$
| Compound No. | X | Ar |
|---|---|---|
| 14 | —CN | 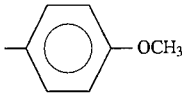 4-OCH₃-C₆H₄— |
| 15 | —CN | 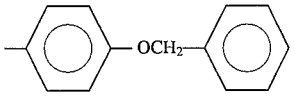 4-OCH₂C₆H₅-C₆H₄— |
| 16 | —CN | 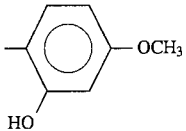 3-HO-4-OCH₃-C₆H₃— |
| 17 | —CN | 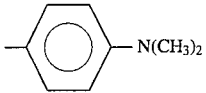 4-N(CH₃)₂-C₆H₄— |
| 18 | —CN | 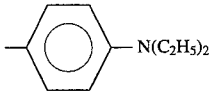 4-N(C₂H₅)₂-C₆H₄— |
| 19 | —CN | 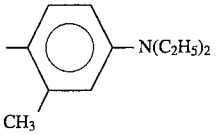 3-CH₃-4-N(C₂H₅)₂-C₆H₃— |
| 20 | —CN | 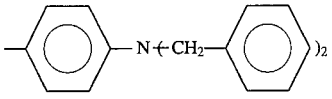 4-N(CH₂C₆H₅)₂-C₆H₄— |
| 21 | —CN | 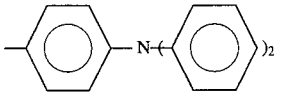 4-N(C₆H₅)₂-C₆H₄— |
| 22 | —CN | 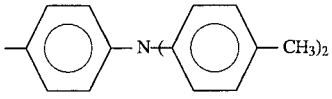 4-N(4-CH₃-C₆H₄)₂-C₆H₄— |
| 23 | —CN | 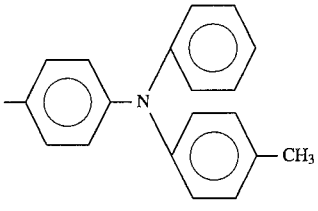 |
| 24 | —CN | 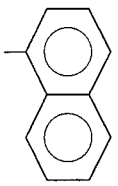 naphthyl— |

TABLE 1-continued
$$Ar-CH=\underset{\underset{X}{|}}{C}-CN \quad (I)$$
| Compound No. | X | Ar |
|---|---|---|
| 25 | —CN | 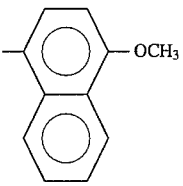 1-methoxynaphthalen-4-yl (OCH₃-substituted naphthalene) |
| 26 | —CN | 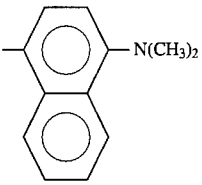 4-(dimethylamino)naphthalen-1-yl |
| 27 | —CN | 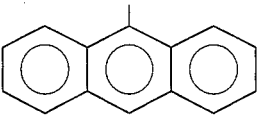 anthracen-9-yl |
| 28 | —CN | 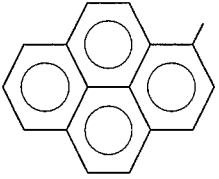 pyrenyl |
| 29 | —CN | 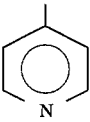 pyridin-4-yl |
| 30 | —CN | 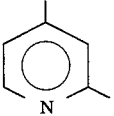 2-methylpyridin-4-yl |
| 31 | —CN | 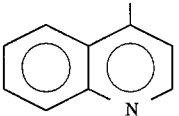 quinolin-4-yl |
| 32 | —CN | 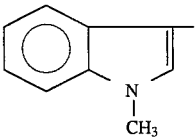 1-methylindol-3-yl |
| 33 | —CN | 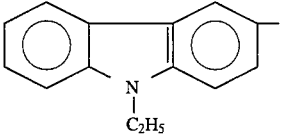 9-ethylcarbazol-3-yl |
| 34 | —CN | 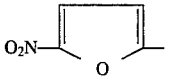 5-nitrofuran-2-yl (O₂N-furan) |

TABLE 1-continued $$Ar-CH=\underset{\underset{X}{|}}{\overset{CN}{C}} \quad (I)$$

| Compound No. | X | Ar |
|---|---|---|
| 35 | —CN | 2,5-dimethylfuran-yl (CH₃-furan-O) |
| 36 | —CN | ferrocenyl (cyclopentadienyl-Fe-cyclopentadienyl) |
| 37 | —COOC₂H₅ | 4-NO₂-C₆H₄— |
| 38 | —COOC₂H₅ | 4-CN-C₆H₄— |
| 39 | —COOC₂H₅ | 2-Cl-3-NO₂-C₆H₃— |
| 40 | —COOC₂H₅ | 4-Cl-C₆H₄— |
| 41 | —COOC₂H₅ | 4-Br-C₆H₄— |
| 42 | —COOC₂H₅ | C₆H₅— |
| 43 | —COOC₂H₅ | 4-(COCH₃)-C₆H₄— |
| 44 | —COOC₂H₅ | 4-C₄H₉-C₆H₄— |
| 45 | —COOC₂H₅ | 4-CF₃-C₆H₄— |
| 46 | —COOC₂H₅ | 4-(OCH₂C₆H₅)-C₆H₄— |
| 47 | —COOC₂H₅ | 4-N(C₂H₅)₂-C₆H₄— |

TABLE 1-continued
$$Ar-CH=\underset{\underset{X}{|}}{\overset{\overset{CN}{|}}{C}}-X \qquad (I)$$
| Compound No. | X | Ar |
|---|---|---|
| 48 | —COOC$_2$H$_5$ | 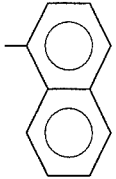 |
| 49 | —COOC$_2$H$_5$ | 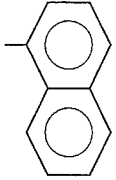 |
| 50 | —COOC$_2$H$_5$ | 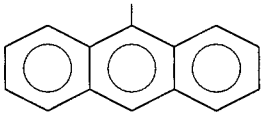 |
| 51 | —COOC$_2$H$_5$ | 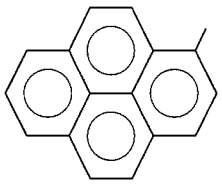 |
| 52 | —COOC$_2$H$_5$ | 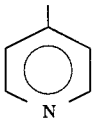 |
| 53 | —COOC$_2$H$_5$ | 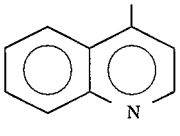 |
| 54 | —COOC$_4$H$_9$ | 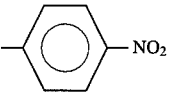 |
| 55 | —COOC$_4$H$_9$ | 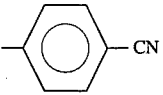 |
| 56 | —COOC$_4$H$_9$ | 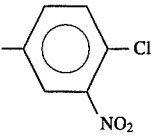 |
| 57 | —COOC$_4$H$_9$ | 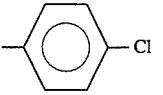 |

TABLE 1-continued $$Ar-CH=\underset{\underset{X}{|}}{\overset{\overset{CN}{|}}{C}}-X \quad (1)$$

| Compound No. | X | Ar |
|---|---|---|
| 58 | —COOC$_4$H$_9$ | 2,4-dichlorophenyl |
| 59 | —COOC$_4$H$_9$ | 4-bromophenyl |
| 60 | —COOC$_4$H$_9$ | 4-acetylphenyl (—C(=O)CH$_3$) |
| 61 | —COOC$_4$H$_9$ | 4-ethylphenyl (—C$_2$H$_5$) |
| 62 | —COOC$_4$H$_9$ | 4-(trifluoromethyl)phenyl (—CF$_3$) |
| 63 | —COOC$_4$H$_9$ | 4-(benzyloxy)phenyl (—OCH$_2$C$_6$H$_5$) |
| 64 | —COOC$_4$H$_9$ | 3-hydroxy-4-methoxyphenyl (HO, —OCH$_3$) |
| 65 | —COOC$_4$H$_9$ | 4-(diethylamino)phenyl (—N(C$_2$H$_5$)$_2$) |
| 66 | —COOC$_4$H$_9$ | 4-(dibenzylamino)phenyl (—N(CH$_2$C$_6$H$_5$)$_2$) |
| 67 | —COOC$_4$H$_9$ | 4-(diphenylamino)phenyl (—N(C$_6$H$_5$)$_2$) |
| 68 | —COOC$_4$H$_9$ | 4-[di(4-methylphenyl)amino]phenyl (—N(C$_6$H$_4$CH$_3$)$_2$) |
| 69 | —COOC$_4$H$_9$ | naphthyl |

TABLE 1-continued $$Ar-CH=C(CN)-X \quad (I)$$

| Compound No. | X | Ar |
|---|---|---|
| 70 | —COOC₄H₉ | 4-methoxynaphth-1-yl (naphthalene with OCH₃) |
| 71 | —COOC₄H₉ | 4-(dimethylamino)naphth-1-yl (naphthalene with N(CH₃)₂) |
| 72 | —COOC₄H₉ | anthracen-9-yl |
| 73 | —COOC₄H₉ | phenanthren-9-yl |
| 74 | —COOC₄H₉ | pyren-1-yl |
| 75 | —COOC₄H₉ | pyridin-4-yl |
| 76 | —COOC₄H₉ | quinolin-4-yl |
| 77 | —COOC₄H₉ | 1-methylindol-2-yl |
| 78 | —COOC₄H₉ | 9-ethylcarbazol-3-yl |

TABLE 1-continued $$Ar-CH=C(CN)-X \quad (I)$$

| Compound No. | X | Ar |
|---|---|---|
| 79 | —COOC$_4$H$_9$ | 5-nitro-2-furyl (O$_2$N-furan) |
| 80 | —COOC$_4$H$_9$ | 5-methyl-2-furyl (CH$_3$-furan) |
| 81 | —COOC$_4$H$_9$ | ferrocenyl (Fe) |
| 82 | —COOCH$_2$CH(CH$_3$)$_2$ | 4-NO$_2$-C$_6$H$_4$— |
| 83 | —COOCH$_2$CH(CH$_3$)$_2$ | 4-CN-C$_6$H$_4$— |
| 84 | —COOCH$_2$CH(CH$_3$)$_2$ | 3-Cl-4-NO$_2$-C$_6$H$_3$— |
| 85 | —COOCH$_2$CH(CH$_3$)$_2$ | 4-Cl-C$_6$H$_4$— |
| 86 | —COOCH$_2$CH(CH$_3$)$_2$ | 4-COCH$_3$-C$_6$H$_4$— |
| 87 | —COOCH$_2$CH(CH$_3$)$_2$ | 4-C$_2$H$_5$-C$_6$H$_4$— |
| 88 | —COOCH$_2$CH(CH$_3$)$_2$ | 4-CF$_3$-C$_6$H$_4$— |
| 89 | —COOCH$_2$CH(CH$_3$)$_2$ | 4-OCH$_2$C$_6$H$_5$-C$_6$H$_4$— |
| 90 | —COOCH$_2$CH(CH$_3$)$_2$ | 4-N(C$_2$H$_5$)$_2$-C$_6$H$_4$— |
| 91 | —COOCH$_2$CH(CH$_3$)$_2$ | 4-N(CH$_2$C$_6$H$_5$)$_2$-C$_6$H$_4$— |
| 92 | —COOCH$_2$CH(CH$_3$)$_2$ | 4-N(C$_6$H$_5$)$_2$-C$_6$H$_4$— |

TABLE 1-continued $$Ar-CH=\underset{\underset{X}{|}}{C}-X \quad \text{(I)} \quad \overset{CN}{}$$

(Structure shows CN on the C)

| Compound No. | X | Ar |
|---|---|---|
| 93 | —COOCH$_2$CH(CH$_3$)$_2$ | naphthyl |
| 94 | —COOCH$_2$CH(CH$_3$)$_2$ | naphthyl-N(CH$_3$)$_2$ |
| 95 | —COOCH$_2$CH(CH$_3$)$_2$ | anthracenyl |
| 96 | —COOCH$_2$CH(CH$_3$)$_2$ | phenanthrenyl |
| 97 | —COOCH$_2$CH(CH$_3$)$_2$ | pyrenyl |
| 98 | —COOCH$_2$CH(CH$_3$)$_2$ | quinolinyl |
| 99 | —COOCH$_2$CH(CH$_3$)$_2$ | N-methylindolyl |
| 100 | —COOCH$_2$CH(CH$_3$)$_2$ | N-ethylcarbazolyl |
| 101 | —COOCH$_2$CH(CH$_3$)$_2$ | O$_2$N-furyl |

TABLE 1-continued
$$Ar-CH=C(CN)-X \quad (I)$$
| Compound No. | X | Ar |
|---|---|---|
| 102 | —COOCH$_2$CH(CH$_3$)$_2$ |  |
TABLE 2
$$Ar-CH=C(COOR)_2 \quad (II)$$
| Compound No. | R | Ar |
|---|---|---|
| 103 | —CH$_3$ |  |
| 104 | —CH$_3$ | 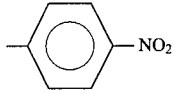 |
| 105 | —CH$_3$ | 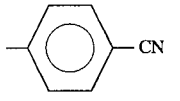 |
| 106 | —CH$_3$ | 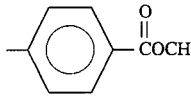 |
| 107 | —CH$_3$ | 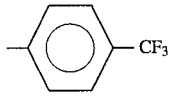 |
| 108 | —CH$_3$ | 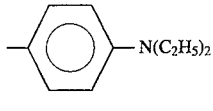 |
| 109 | —CH$_3$ | 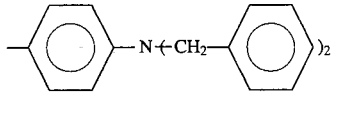 |
| 110 | —CH$_3$ | 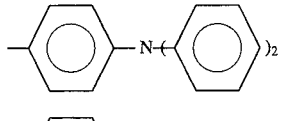 |
| 111 | —CH$_3$ | 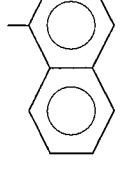 |
TABLE 2-continued
$$Ar-CH=C(COOR)_2 \quad (II)$$
| Compound No. | R | Ar |
|---|---|---|
| 112 | —CH$_3$ | 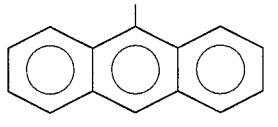 |
| 113 | —CH$_3$ | 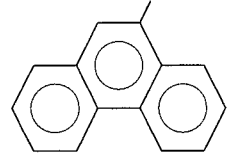 |
| 114 | —CH$_3$ | 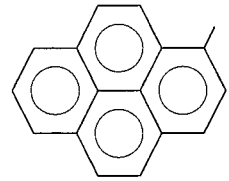 |
| 115 | —CH$_3$ | 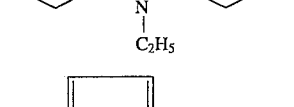 |
| 116 | —C$_4$H$_9$ | 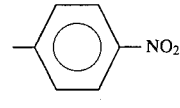 |
| 117 | —C$_4$H$_9$ | 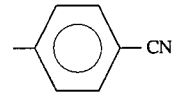 |
| 118 | —C$_4$H$_9$ | 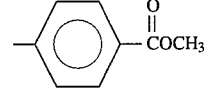 |
| 119 | —C$_4$H$_9$ | 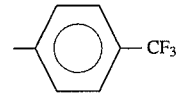 |
| 120 | —C$_4$H$_9$ | 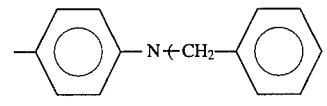 |

TABLE 2-continued $Ar-CH=C(COOR)_2$ (II)

| Compound No. | R | Ar |
|---|---|---|
| 121 | $-C_4H_9$ | phenyl-N(phenyl)₂ |
| 122 | $-C_4H_9$ | naphthyl |
| 123 | $-C_4H_9$ | anthryl |
| 124 | $-C_4H_9$ | phenanthryl |
| 125 | $-C_4H_9$ | pyrenyl |
| 126 | $-C_4H_9$ | N-ethylcarbazolyl |
| 127 | $-C_4H_9$ | 5-nitrofuran-2-yl |
| 128 | $-C(CH_3)_2$ | 4-nitrophenyl |
| 129 | $-C(CH_3)_2$ | 4-cyanophenyl |
| 130 | $-C(CH_3)_2$ | 4-(N,N-dibenzylamino)phenyl |
| 131 | $-C(CH_3)_2$ | naphthyl |
| 132 | $-C(CH_3)_2$ | anthryl |
| 133 | $-C(CH_3)_2$ | phenanthryl |
| 134 | $-C(CH_3)_2$ | pyrenyl |
| 135 | $-C(CH_3)_2$ | N-ethylcarbazolyl |
| 136 | $-C(CH_3)_2$ | 5-nitrofuran-2-yl |

The vinylidene compounds of formulas (I) and (II) for use in the present invention can be obtained by allowing an aromatic aldehyde compound of formula (III) to react with a malonic acid derivative of formula (IV) in the presence of a basic catalyst.

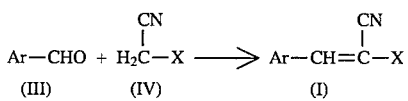

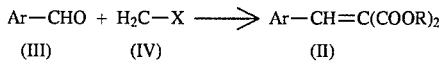

Specific examples of the basic catalyst for use in the above-mentioned reaction are an organic base such as pyridine, piperidine, or triethylamine; a salt of acetic acid such as sodium acetate, potassium acetate or ammonium acetate; and an inorganic base such as sodium hydroxide, potassium hydroxide, sodium carbonate or potassium carbonate.

The above-mentioned reaction for preparing of the vinylidene compounds of formulas (I) and (II) can be carried out without a solvent or in a polar solvent such as methanol, ethanol, tetrahydrofuran, 1,4-dioxane or N,N-dimethylformamide. The reaction temperature can be set in the range of from room temperature to 150° C., preferably in the range of from room temperature to 100° C.

The structure of the photoconductor of the present invention will now be explained making reference to FIGS. 1 to 3.

A photoconductor shown in FIG. 1 comprises a substrate 1 and a laminate-type photoconductive layer 4 formed on the substrate 1 which is an electroconductive substrate or prepared by providing an electroconductive layer on a sheet. The above-mentioned photoconductive layer 4 consists of a charge generation layer 2 comprising a charge generating material and if necessary a binder resin, and a charge transport layer 3 formed on the charge generation layer 2, comprising a charge transporting material and if necessary a binder resin.

Figure 2:
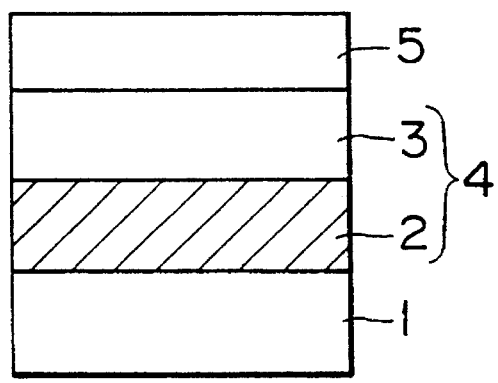
FIG. 2 is a schematic cross-sectional view showing a second example of an electrophotographic photoconductor according to the present invention.

The photoconductor shown in FIG. 2 further comprises a protective layer 5 provided on a photoconductive layer 4.

Figure 3:
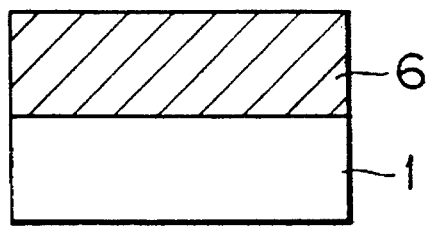
FIG. 3 is a schematic cross-sectional view showing a third example of an electrophotographic photoconductor according to the present invention.

FIG. 3 shows a cross-sectional view of a photoconductor which comprises a single-layered type photoconductive layer 6 formed on a substrate 1, comprising a charge generating material, a charge transporting material, and if necessary a binder resin. A protective layer can also be provided on the single-layered type photoconductive layer 6, or an intermediate layer may be interposed between the substrate 1 and the photoconductive layer 4 or 6.

When the electrophotographic photoconductor of the present invention comprises a laminate-type photoconductive layer, as shown in FIGS. 1 and 2, the charge transporting material is dissolved or dispersed singly in an appropriate solvent or in combination with an appropriate binder resin to obtain a coating liquid for a charge transport layer. The thus obtained coating liquid is coated on a charge generation layer and dried, so that the charge transport layer is formed on the charge generation layer.

Specific examples of the binder resin for the photoconductive layer for use in the present invention are addition polymerization type resins, polyaddition type resins, and polycondensation type resins, such as polyethylene, polypropylene, acrylic resin, methacrylic resin, vinyl chloride resin, vinyl acetate resin, epoxy resin, polyurethane resin, phenolic resin, polyester resin, alkyd resin, polycarbonate resin, silicone resin, and melamine resin; copolymerization type resins which comprise two or more repeat units in the above-mentioned resins, such as insulating resins of vinyl chloride - vinyl acetate copolymer resin and vinyl chloride - vinyl acetate - maleic anhydride copolymer resin; and polymeric semiconductors such as poly-N-vinylcarbazole.

Specific examples of the solvent used in preparing the charge transport layer are N,N-dimethylformamide, toluene, xylene, monochlorobenzene, 1,2-dichloroethane, dichloromethane, 1,1,1-trichloroethane, 1,1,2-trichloroethylene, tetrahydrofuran, methyl ethyl ketone, cyclohexanone, ethyl acetate, and butyl acetate.

It is preferable that 20 to 200 parts by weight of the charge transporting material and 100 parts by weight of the binder resin be contained in the charge transport layer.

It is also preferable that the thickness of the charge transport layer be 5 to 50 μm, more preferably 5 to 30 μm.

In the present invention, the charge generation layer can be formed by vacuum-depositing the charge generating material on the electroconductive substrate. Alternatively, the charge generating material is dissolved or dispersed singly in an appropriate solvent or in combination with an appropriate binder resin to obtain a coating liquid for the charge generation layer, and the thus obtained coating liquid is coated on the electroconductive substrate and dried.

When the charge generation layer is formed by coating a dispersion of the charge generating material, it is preferable that the average particle size of the charge generating material be within the range from 0.01 μm to 1 μm.

When the particle size of the charge generating material is 2 μm or less, the charge generating material can be uniformly dispersed in the solvent, and part of the particles can be prevented from protruding over the surface of the charge generation layer, so that the surface smoothness is not impaired. Therefore, electrical discharge which takes place on the particle-protruded portion can be prevented, and the toner filming phenomenon, which is an adhesion of toner particles thereon, does not occur.

In addition, when the particle size of the charge generating material is 0.01 μm or more, the particles do not tend to aggregate. As a result, an increase of the resistivity of the charge generation layer and a decrease of the photosensitivity of the photoconductor can be prevented, so that the photoconductor can be repeatedly used.

To prepare the charge generation layer, the charge generating material is dispersed in the form of finely-divided particles in the solvent in a ball mill or a homomixer. Then, finely-divided particles of the charge generating material are mixed with a binder resin and dispersed to obtain a coating liquid for the charge generation layer, and the thus obtained coating liquid is coated on the substrate. In this method of forming the charge generation layer, it is preferable that the particles of the charge generating material be dispersed with the application of supersonic wave thereto so as to obtain a uniform dispersion.

As the charge generating material for use in the electrophotographic photoconductor according to the present invention, any inorganic or organic materials which can absorb visible light and generate free charges can be employed.

Specific examples of such materials are inorganic materials such as amorphous selenium, trigonal-system selenium, selenium - arsenic alloy, selenium - tellurium alloy, cadmium sulfide, cadmium selenide, cadmium sulfoselenide, mercury sulfide, lead oxide, lead sulfide, and amorphous silicone; and organic materials such as bisazo dye, polyazo dye, triarylmethane dye, thiazine dye, oxazine dye, xanthene dye, cyanine dye, styryl dye, pyrylium dye, quinacridone dye, indigo dye, perylene dye, polycyclic quinone dye, bisbenzimidazole dye, indanthrone dye, squarylium dye, anthraquinone dye, and phthalocyanine dye.

It is preferable that 20 to 200 parts by weight of the charge generating material and 100 parts by weight of the binder resin be contained in the charge generation layer.

It is also preferable that the thickness of the charge generation layer be 0.1 to 10 μm, more preferably 0.5 to 5 μm.

In the case where the electrophotographic photoconductor of the present invention comprises a single-layered type photoconductive layer, as shown in FIG. 3, it is preferable that 20 to 200 parts by weight of the charge generating material, 20 to 200 parts by weight of the charge transporting material and 100 parts by weight of the binder resin be contained in the photoconductive layer.

It is also preferable that the thickness of the single-layered type photoconductive layer be 7 to 50 μm, more preferably 10 to 30 μm.

Examples of the materials for the electroconductive substrate for use in the present invention are a sheet, drum or foil of metals such as aluminum and nickel; a plastic film on which aluminum, tin oxide, or indium oxide is deposited; and a film or drum of paper or plastic which is coated by an electroconductive material.

Furthermore, the previously mentioned intermediate layer which can be interposed between the substrate and the photoconductive layer functions as an adhesive layer or a barrier layer.

Specific examples of the material for the intermediate layer for use in the present invention are the same resins as used in preparing the photoconductive layer as the binder resins, and resins such as polyvinyl alcohol, ethyl cellulose, carboxymethyl cellulose, vinyl chloride - vinyl acetate copolymer, vinyl chloride - vinyl acetate - maleic anhydride copolymer, casein, and N-alkoxymethyl nylon. In addition to the above, tin oxide or indium may be dispersed in one of the above-mentioned resins. A film prepared by deposition of aluminum oxide, zinc oxide, or silicon oxide can also be employed.

It is preferable that the thickness of the intermediate layer be 1 µm or less.

As the materials for the previously mentioned protective layer, the above-mentioned resins are used as they are, or a material with a low resistivity such as tin oxide or indium oxide may be dispersed in the above-mentioned resins. In addition to the above, an organic plasma polymerization film can be used as the protective layer. In this case, the organic plasma polymerization film may comprise oxygen, nitrogen, halogen, or an atom belonging to the group III or the group V in the periodic table when necessary.

Other features of this invention will become apparent in the course of the following description of exemplary embodiments, which are given for illustration of the invention and are not intended to be limiting thereof.

the reaction mixture to obtain a crude material.

The thus obtained material was recrystallized from ethanol, whereby 4.57 g of 4-nitrobenzalmalononitrile (Compound No. 1) was obtained in pure form.

The melting point of the above obtained compound was 160.5° to 162.0° C.

Figure 4:
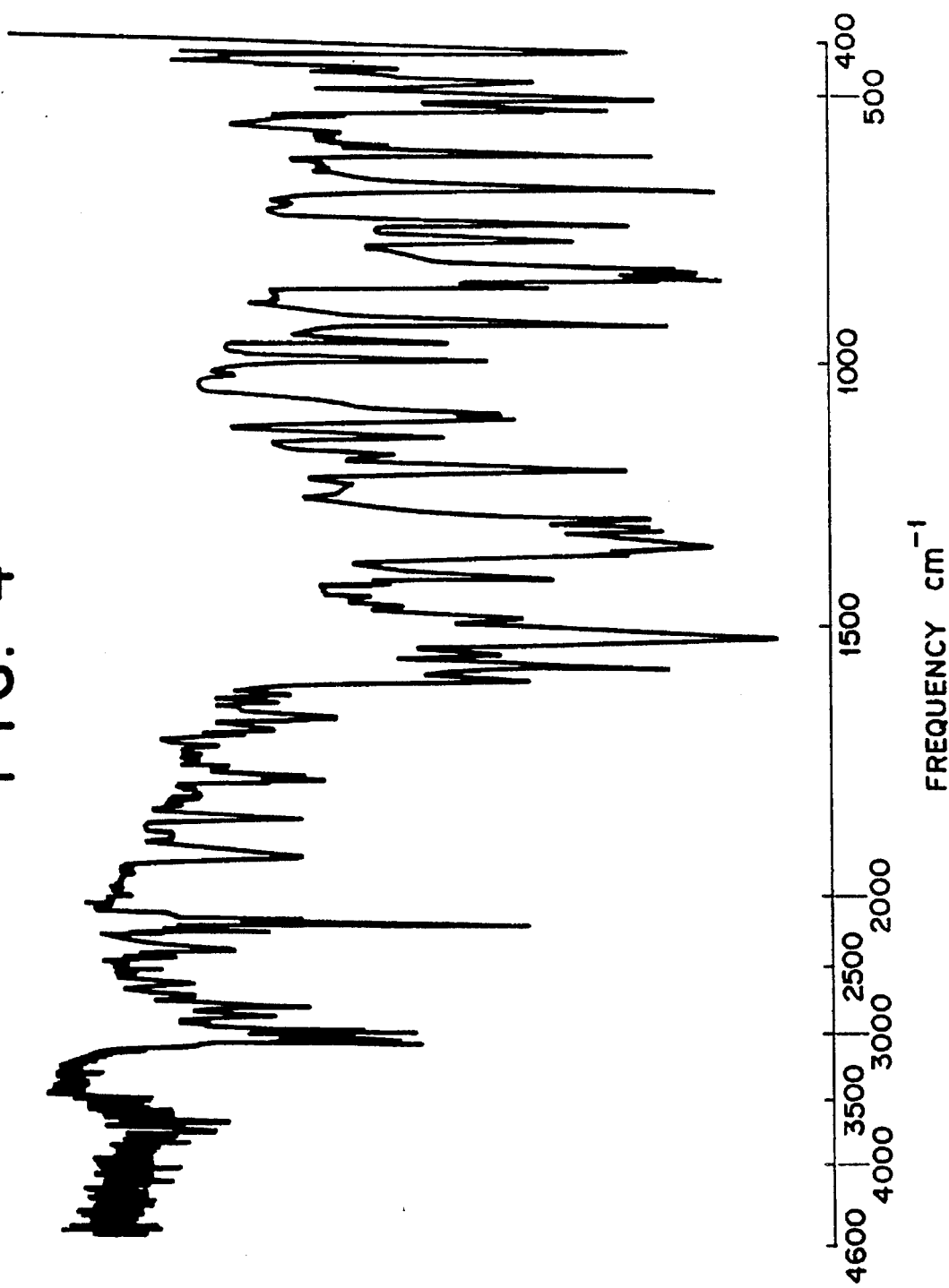
FIG. 4 is an IR absorption spectrum of 4-nitrobenzalmalononitrile for use in Example 1.

FIG. 4 shows an IR absorption spectrum of the above compound.

Synthesis Examples 2 to 28

The same procedure for preparation of the 4-nitrobenzalmalononitrile in Synthesis Example 1 was repeated except that the 4-nitrobenzaldehyde and malononitrile used in Synthesis Example 1 were respectively replaced by various kinds of aromatic aldehyde compounds of formula (III) and various kinds of malonic acid derivatives of formula (IV), so that vinylidene compounds of formulas (I) and (II) shown in Table 3 were obtained. The melting point and the results of elemental analysis of each product are also shown in Table 3.

TABLE 3

| Synthesis Example | Compound No. | Melting Point (°C.) | Elemental Analysis (%) | | |
|---|---|---|---|---|---|
| | | | C Found (Calculated) | H Found (Calculated) | N Found (Calculated) |
| Example 1 | 1 | 160.5–162.0 | 60.410 (60.306) | 2.605 (2.531) | 21.208 (21.098) |
| Example 2 | 3 | 156.0–156.5 | 73.895 (73.736) | 2.779 (2.813) | 23.565 (23.452) |
| Example 3 | 17 | 182.0–183.0 | 73.058 (73.074) | 5.559 (5.622) | 21.250 (21.304) |
| Example 4 | 24 | 168.6–169.5 | 82.486 (82.335) | 3.886 (3.948) | 13.716 (13.717) |
| Example 5 | 27 | 210.5–211.3 | 85.112 (85.020) | 3.843 (3.964) | 11.041 (11.016) |
| Example 6 | 28 | 254.0–254.5 | 86.417 (86.313) | 3.561 (3.622) | 10.169 (10.066) |
| Example 7 | 31 | 145.5–146.5 | 75.979 (76.086) | 3.557 (3.438) | 20.320 (20.476) |
| Example 8 | 34 | 178.5–179.0 | 50.872 (50.805) | 1.574 (1.599) | 22.390 (22.218) |
| Example 9 | 36 | 98.0–99.0 | 63.491 (63.432) | 3.700 (3.802) | 10.560 (10.568) |
| Example 10 | 37 | 167.5–168.0 | 58.575 (58.537) | 3.973 (4.094) | 11.420 (11.378) |
| Example 11 | 54 | 124.0–125.0 | 61.476 (61.308) | 5.054 (5.145) | 10.296 (10.214) |
| Example 12 | 55 | 128.0–128.5 | 68.580 (68.689) | 5.506 (5.380) | 10.415 (10.681) |
| Example 13 | 66 | 150.5–151.7 | 79.302 (79.216) | 6.522 (6.648) | 6.711 (6.599) |
| Example 14 | 72 | 125.0–125.5 | 80.396 (80.219) | 5.791 (5.814) | 4.167 (4.252) |
| Example 15 | 74 | 99.5–100.0 | 81.711 (81.564) | 5.274 (5.419) | 3.913 (3.963) |
| Example 16 | 78 | 173.7–174.5 | 76.342 (76.276) | 6.249 (6.401) | 8.024 (8.086) |
| Example 17 | 79 | 129.0–130.0 | 54.658 (54.546) | 4.569 (4.578) | 10.563 (10.602) |
| Example 18 | 81 | 130.5–131.3 | 63.650 (63.550) | 5.399 (5.630) | 4.106 (4.117) |
| Example 19 | 82 | 141.0–141.8 | 61.337 (61.308) | 5.049 (5.145) | 10.282 (10.214) |
| Example 20 | 83 | 146.0–146.5 | 68.742 (68.689) | 5.376 (5.380) | 10.617 (10.681) |
| Example 21 | 95 | 78.0–79.5 | 80.348 (80.219) | 5.760 (5.814) | 4.227 (4.252) |
| Example 22 | 96 | 101.0–102.0 | 80.273 (80.219) | 5.747 (5.814) | 4.239 (4.252) |
| Example 23 | 97 | 122.0–123.0 | 81.626 (81.564) | 5.375 (5.419) | 3.929 (3.963) |
| Example 24 | 100 | 124.0–125.5 | 76.257 (76.276) | 6.308 (6.401) | 8.121 (8.086) |
| Example 25 | 101 | 134.0–135.0 | 54.642 (54.546) | 4.635 (4.578) | 10.597 (10.602) |
| Example 26 | 103 | 87.5–89.0 | 54.251 (54.344) | 4.102 (4.181) | 5.176 (5.281) |
| Example 27 | 111 | 104.5–105.3 | 75.034 (74.988) | 4.956 (5.035) | — |
| Example 28 | 128 | 213.0–214.0 | 56.388 (56.322) | 3.987 (4.000) | 4.940 (5.052) |

Synthesis Example 1

[Synthesis of 4-nitrobenzalmalononitrile (Compound No. 1)]

A mixture of 4.53 g of commercially available 4-nitrobenzaldehyde, 2.97 g of malononitrile, and two drops of piperidine was refluxed in 100 ml of methanol for 4 hours. After the completion of the reaction, the thus obtained reaction mixture was cooled, so that a solid product was formed in the reaction mixture. The solid product was separated from

EXAMPLE 1

[Formation of Charge Generation Layer]

5 parts by weight of a bisazo dye of formula (A), 2.5 parts by weight of a commercially available butyral resin (Trademark "Denka Butyral Resin #3000-2", made by Denki Kagaku Kogyo K.K.), and 92.5 parts by weight of tetrahydrofuran were dispersed in a ball mill for 12 hours.

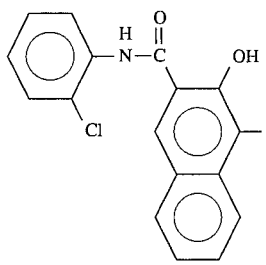 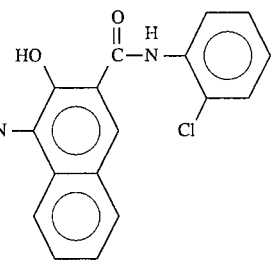 (A)

Tetrahydrofuran was further added to the thus obtained mixture in such an amount that the obtained dispersion might have a concentration of 2 wt. %, and the above mixture was dispersed again to prepare a coating liquid for a charge generation layer. The thus obtained coating liquid was coated by a doctor blade on an aluminum-deposited surface of an aluminum-deposited polyester film with a thickness of 100 μm serving as a substrate, and dried, so that a charge generation layer with a thickness of 1.0 μm was formed on the substrate.

[Formation of Charge Transport Layer]

6 parts by weight of the Compound No. 1 prepared in Synthesis Example 1, 10 parts by weight of a polycarbonate resin (Trademark "K-1300", made by Teijin Chemicals Ltd.), 0.002 parts by weight of a methylphenyl - silicone (Trademark "KF50 100CPS", made by Sin-Etsu Chemical Co,. Ltd.), and 94 parts by weight of tetrahydrofuran were mixed to prepare a coating liquid for a charge transport layer. The thus obtained coating liquid was coated by the doctor blade on the above obtained charge generation layer, and dried, so that a charge transport layer with a thickness of 20.0 μm was formed on the charge generation layer. Thus, a laminate-type electrophotographic photoconductor No. 1 comprising an aluminum electroconductive substrate, the charge generation layer and the charge transport layer of the present invention was obtained.

EXAMPLES 2 to 13

The procedure for preparation of the electrophotographic photoconductor No. 1 in Example 1 was repeated except that the Compound No. 1 for use in the coating liquid for the charge transport layer in Example 1 was replaced by each of the vinylidene compounds shown in Table 1, whereby laminate-type electrophotographic photoconductors No. 2 to No. 13 of the present invention was obtained.

EXAMPLE 14

The procedure for preparation of the electrophotographic photoconductor No. 1 in Example 1 was repeated except that 5 parts by weight of the bisazo dye of formula (A) for use in the coating liquid for the charge generation layer and the Compound No. 1 for use in the coating liquid for the charge transport layer used in Example 1 were respectively replaced by 6 parts by weight of a trisazo dye of formula (B) and the Compound No. 3 prepared in Synthesis Example 2 shown in Table 3, whereby a laminate-type electrophotographic photoconductor No. 14 of the present invention was obtained.

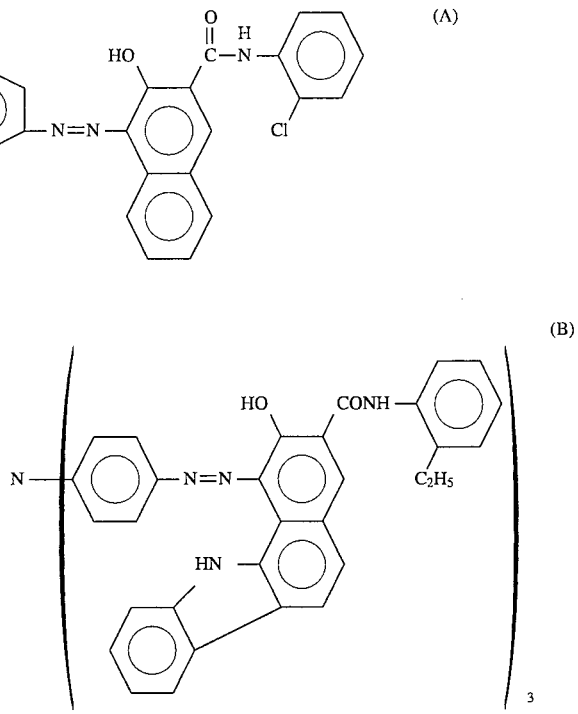

EXAMPLES 15 to 31

The procedure for preparation of the electrophotographic photoconductor No. 14 in Example 14 was repeated except that the Compound No. 3 for use in the coating liquid for the charge transport layer used in Example 14 was replaced by each of the vinylidene compounds shown in Table 3, whereby laminate-type electrophotographic photoconductors No. 15 to No. 31 of the present invention were obtained.

EXAMPLE 32

[Formation of Charge Generation Layer]

A mixture of 5 parts by weight of titanylphthalocyanine (TiPc), 5 parts by weight of a polyvinyl butyral resin (Trademark "S-Lec BLS", made by Sekisui Chemical Co., Ltd.), and 90 parts by weight of tetrahydrofuran was dispersed in a ball mill for 12 hours. Tetrahydrofuran was further added to the thus obtained mixture in such an amount that the obtained dispersion might have a concentration of 2 wt. %, and the above mixture was dispersed again to prepare a coating liquid for a charge generation layer. The thus obtained coating liquid was coated by a doctor blade on an aluminum-deposited surface of an aluminum-deposited polyester film with a thickness of 100 μm serving as a substrate, and dried, so that a charge generation layer with a thickness of 0.5 μm was formed on the substrate.

[Formation of Charge Transport Layer]

6 parts by weight of the Compound No. 24 prepared in Synthesis Example 4 shown in Table 3, 10 parts by weight of a polycarbonate resin (Trademark "K-1300", made by Teijin Chemicals Ltd.), and 94 parts by weight of tetrahydrofuran were mixed to prepare a coating liquid for a charge transport layer. The thus obtained coating liquid was coated on the above obtained charge generation layer by the doctor blade, and dried, so that a charge transport layer with a thickness of 20.0 μm was formed on the charge generation layer. Thus, a laminate-type electrophotographic photoconductor No. 32 comprising an aluminum electroconductive substrate, the charge generation layer and the charge transport layer of the present invention was obtained.

EXAMPLES 33 to 42

The procedure for preparation of the electrophotographic photoconductor No. 32 in Example 32 was repeated except that the Compound No. 24 for use in the coating liquid for the charge transport layer used in Example 32 was replaced by each of the vinylidene compounds shown in Table 3, whereby laminate-type electrophotographic photoconductors No. 33 to No. 42 of the present invention were obtained.

Each of the thus prepared electrophotographic photoconductors No. 1 to No. 42 according to the present invention was positively charged under application of +6 kV of corona charge, using a commercially available electrostatic copying sheet testing apparatus ("SP-428", made by Kawaguchi Electro Works Co., Ltd.). Then, each electrophotographic photoconductor was allowed to stand in the dark for 20 seconds without applying any charge thereto, and the surface potential Vo (V) of the photoconductor was measured. Each photoconductor was then illuminated by a tungsten lamp in such a manner that the illuminance on the illuminated surface of the photoconductor was 40 lux, and the exposure $E_{1/2}$ (lux.sec) required to reduce the initial surface potential Vo (V) to ½ thereof was measured. The results are shown in Table 4.

TABLE 4

| Example No. | Photo-conductor No. | Charge Generating Material | Compound No. | Vo (V) | $E_{1/2}$ (lux · sec) |
|---|---|---|---|---|---|
| Ex. 1 | 1 | A | 1 | 1192 | 52.3 |
| Ex. 2 | 2 | A | 24 | 1761 | 63.9 |
| Ex. 3 | 3 | A | 31 | 1765 | 115.8 |
| Ex. 4 | 4 | A | 37 | 736 | 22.8 |
| Ex. 5 | 5 | A | 54 | 1892 | 25.8 |
| Ex. 6 | 6 | A | 55 | 1633 | 29.4 |
| Ex. 7 | 7 | A | 74 | 1850 | 12.2 |
| Ex. 8 | 8 | A | 79 | 1817 | 43.1 |
| Ex. 9 | 9 | A | 82 | 2281 | 26.1 |
| Ex. 10 | 10 | A | 83 | 2247 | 22.1 |
| Ex. 11 | 11 | A | 96 | 2431 | 23.8 |
| Ex. 12 | 12 | A | 97 | 1762 | 31.7 |
| Ex. 13 | 13 | A | 101 | 2183 | 76.1 |
| Ex. 14 | 14 | B | 3 | 1830 | 95.7 |
| Ex. 15 | 15 | B | 24 | 1578 | 76.2 |
| Ex. 16 | 16 | B | 27 | 1887 | 48.0 |
| Ex. 17 | 17 | B | 34 | 1909 | 121.4 |
| Ex. 18 | 18 | B | 37 | 558 | 14.5 |
| Ex. 19 | 19 | B | 54 | 1416 | 43.1 |
| Ex. 20 | 20 | B | 55 | 1248 | 30.6 |
| Ex. 21 | 21 | B | 66 | 1976 | 145.6 |
| Ex. 22 | 22 | B | 72 | 2104 | 68.1 |
| Ex. 23 | 23 | B | 74 | 1726 | 25.7 |
| Ex. 24 | 24 | B | 79 | 1913 | 63.2 |
| Ex. 25 | 25 | B | 82 | 1628 | 54.3 |
| Ex. 26 | 26 | B | 83 | 2043 | 38.9 |
| Ex. 27 | 27 | B | 95 | 2187 | 128.4 |
| Ex. 28 | 28 | B | 96 | 2262 | 47.2 |
| Ex. 29 | 29 | B | 97 | 1956 | 35.0 |
| Ex. 30 | 30 | B | 100 | 2252 | 150.7 |
| Ex. 31 | 31 | B | 101 | 1893 | 76.2 |
| Ex. 32 | 32 | TiPc | 24 | 1424 | 66.0 |
| Ex. 33 | 33 | TiPc | 37 | 719 | 22.4 |
| Ex. 34 | 34 | TiPc | 54 | 1138 | 37.5 |
| Ex. 35 | 35 | TiPc | 55 | 1107 | 25.4 |
| Ex. 36 | 36 | TiPc | 74 | 1720 | 13.9 |
| Ex. 37 | 37 | TiPc | 79 | 1532 | 65.0 |
| Ex. 38 | 38 | TiPc | 82 | 1319 | 36.7 |
| Ex. 39 | 39 | TiPc | 83 | 1829 | 34.1 |
| Ex. 40 | 40 | TiPc | 96 | 1837 | 40.6 |
| Ex. 41 | 41 | TiPc | 97 | 1468 | 26.0 |
| Ex. 42 | 42 | TiPc | 101 | 1799 | 46.1 |

The vinylidene compounds used as the charge transporting materials in the electrophotographic photoconductor of the present invention can be prepared by a relatively simple and effective method, and excellently dissolved or dispersed in a binder resin. Furthermore, the vinylidene compounds can function as charge transporting materials capable of effectively accepting and transporting the electrical charges which are generated in a charge generation layer. Accordingly, the electrophotographic photoconductors comprising the vinylidene compounds as the charge transporting materials according to the present invention have high photosensitivity and high durability, and can readily bring about the dark decay.

What is claimed is:

1. An electrophotographic photoconductor, comprising:
   a) an electroconductive substrate;
   b) a photoconductive layer formed thereon, comprising a charge generating material, and a vinylidene compound serving as a charge transporting material, which is selected from the group consisting of a vinylidene compound of the formula (I):

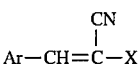

$$Ar—CH=C(CN)—X$$

wherein Ar represents an aromatic group selected from the group consisting of pyrenyl, phenanthrenyl and anthracenyl, and said group substituted by amino, cyano, nitro, alkyl of 1 to 8 carbon atoms, halogen and alkoxycarbonyl of the formula:

$$—COOC_nH_{2n+1}$$

wherein n is an integer of 1 to 8; and a vinylidene compound of the formula (II):

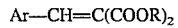

$$Ar—CH=C(COOR)_2$$

wherein Ar represents an aromatic group selected from the group consisting of pyrenyl, phenanthrenyl and anthracenyl, and said groups substituted by amino, cyano, nitro, alkyl of 1 to 8 carbon atoms, halogen and alkoxycarbonyl of the formula:

$$—COOC_nH_{2n+1}$$

wherein n is an integer of 1 to 8, and R is an alkyl group having 1 to 8 carbon atoms, which are unattached or which form a ring in combination together.

2. The electrophotographic photoconductor as claimed in claim 1, wherein said aromatic group represented by Ar in the formula (I) or (II) is pyrenyl.

3. The electrophotographic photoconductor as claimed in claim 1, wherein said amino group is selected from the group consisting of N,N-dimethylamino, N,N-diethylamino, N,N-dibenzylamino, N,N-diphenylamino, N,N-ditolylamino, and N-totyl-N-phenylamino.

4. The electrophotographic photoconductor as claimed in claim 1, wherein said alkyl group having 1 to 8 carbon atoms is selected from the group consisting of methoxy group, ethoxy group and benzyloxy group.

5. The electrophotographic photoconductor as claimed in claim 1, wherein said alkyl group having 1 to 8 carbon atoms is selected from the group consisting of methyl, ethyl, butyl, t-butyl and trifluoromethyl.

6. The electrophotographic photoconductor as claimed in claim 1, wherein said halogen atom is selected from the group consisting of fluorine, chlorine and bromine.

7. The electrophotographic photoconductor as claimed in claim 1, wherein said alkoxycarbonyl group is selected from the group consisting of methoxycarbonyl, ethoxycarbonyl and butoxycarbonyl.

8. The electrophotographic photocondutor as claimed in claim 1, wherein said photoconductive layer further comprises a binder resin.

9. The electrophotographic photoconductor as claimed in claim 8, wherein said binder resin is selected form the group consisting of polyethylene, polypropylene, acrylic resin, methacrylic resin, vinyl chloride resin, vinyl acetate resin, epoxy resin, polyurethane resin, phenolic resin, polyester resin, alkyd resin, polycarbonate resin, silicone resin, melamine resin, vinyl chloride - vinyl acetate copolymer resin, vinyl chloride - vinyl acetate - maleic anhydride copolymer resin, and poly-N-vinylcarbazole.

10. The electrophotographic photoconductor as claimed in claim 8, wherein said photoconductive layer comprises 20 to 200 parts by weight of said charge generating material, 20 to 200 parts by weight of said vinylidene compound serving as a charge transporting material, ad 100 parts by weight of said binder resin.

11. The electrophotographic photocondutor as claimed in claim 10, wherein said photoconductive layer has a thickness of 7 to 50 µm.

12. The electrophotographic photoconductor as claimed in claim 1, wherein said photoconductive layer comprises a charge generation layer comprising said charge generating material and a charge transport layer comprising said vinylidene compound serving as a charge transporting material, with one of said two layers being overlayed on the other.

13. The electrophotographic photoconductor as claimed in claim 12, wherein said charge transport layer further comprises a binder resin.

14. The electrophotographic photoconductor as claimed in claim 13, wherein said charge transport layer comprises 20 to 200 parts by weight of said vinylidene compound serving as a charge transporting material, and 100 parts by weight of said binder agent.

15. The electrophotographic photoconductor as claimed in claim 14, wherein said charge transport layer has a thickness of 5 to 50 µm.

16. The electrophotographic photoconductor as claimed in claim 12, wherein said charge generation layer further comprises a binder agent.

17. The electrophotographic photoconductor as claimed in claim 15, wherein said charge generation layer comprises 20 to 200 parts by weight of said charge generating material, and 100 parts by weight of said binder agent.

18. The electrophotographic photoconductor as claimed in claim 17, wherein said charge generation layer has a thickness of 0.1 to 10 µm.

19. The electrophotographic photoconductor as claimed in claim 12, wherein said charge generating material is selected from the group consisting of amorphous selenium, trigonal-system selenium, selenium - arsenic alloy, selenium - tellurium alloy, cadmium sulfide, lead oxide, lead sulfide, amorphous silicone, bisazo dye, polyazo dye, triarylmethane dye, thiazine dye, oxazine dye, quinacridone dye, indigo dye, perylene dye, polycyclic quinone dye, bisbenzimidazole dye, indanthrone dye, squarylium dye, anthraquinone dye, and phthalocyanine dye.

20. The electrophotographic photoconductor as claimed in claim 1, further comprising a protective layer provided on said photoconductive layer.

21. The electrophotographic photoconductor as claimed in claim 1, further comprising an intermediate layer provided between said electroconductive substrate and said photoconductive layer.

22. The electrophotographic photoconductor as claimed in claim 21, wherein said intermediate layer has a thickness of 1 µm or less.

* * * * *

UNITED STATES PATENT AND TRADEMARK OFFICE
CERTIFICATE OF CORRECTION

PATENT NO. : 5,486,438

DATED : January 23, 1996

INVENTOR(S) : Masayuki SHOSHI, et al.

It is certified that error appears in the above-identified patent and that said Letters Patent is hereby corrected as shown below:

Column 36, line 25, after "cadmium sulfide," insert
--cadmium selenide, cadmium sulfoselenide, mercury sulfide,--;

line 27, after "oxazine dye," insert
--xanthene dye, cyanine dye, styryl dye, pyrylium dye,--.

UNITED STATES PATENT AND TRADEMARK OFFICE
CERTIFICATE OF CORRECTION

PATENT NO. : 5,486,438
DATED : January 23, 1996
INVENTOR(S) : Masayuki SHOSHI, et al.

It is certified that error appears in the above-identified patent and that said Letters Patent is hereby corrected as shown below:

Column 1, line 24, "photoconductors a photoconductive layer" should read --a photoconductive layer--
   line 39, "arid a charge" should read --and a charge--.

Column 35, line 32, "ad 100 parts" should read --and 100 parts--.

Signed and Sealed this

Twenty-sixth Day of May, 1998

Attest:

BRUCE LEHMAN

*Attesting Officer*    *Commissioner of Patents and Trademarks*